(12) United States Patent
Schneider

(10) Patent No.: US 10,494,197 B2
(45) Date of Patent: Dec. 3, 2019

(54) METHODS FOR TRANSFERRING DISCRETE ARTICLES

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 15/993,659

(22) Filed: May 31, 2018

(65) Prior Publication Data

US 2018/0362266 A1   Dec. 20, 2018

Related U.S. Application Data

(60) Provisional application No. 62/520,595, filed on Jun. 16, 2017.

(51) Int. Cl.

| | |
|---|---|
| *B65G 47/84* | (2006.01) |
| *B65G 29/02* | (2006.01) |
| *B65G 47/244* | (2006.01) |
| *B65H 29/24* | (2006.01) |
| *A61F 13/15* | (2006.01) |

(52) U.S. Cl.
CPC ...... *B65G 47/848* (2013.01); *A61F 13/15764* (2013.01); *B65G 29/02* (2013.01); *B65G 47/244* (2013.01); *B65H 29/241* (2013.01); *B65H 2801/57* (2013.01)

(58) Field of Classification Search
CPC ...... B65G 29/00; B65G 29/02; B65G 47/244; B65G 47/848; B65G 47/915; A61F 13/15764; B65H 29/241; B65H 35/08; B65H 39/14; B65H 2801/57
See application file for complete search history.

(56) References Cited

U.S. PATENT DOCUMENTS

| | | | |
|---|---|---|---|
| 5,693,165 A | 12/1997 | Schmitz | |
| 6,620,276 B1 | 9/2003 | Kuntze et al. | |
| 8,377,249 B2 | 2/2013 | Gill | |
| 8,813,351 B2* | 8/2014 | Schoultz | B65H 39/14 29/782 |

(Continued)

OTHER PUBLICATIONS

International Search Report and Written Opinion, PCT/US2018/036825, dated Aug. 14, 2018.

*Primary Examiner* — Gene O Crawford
*Assistant Examiner* — Keith R Campbell
(74) *Attorney, Agent, or Firm* — Christian M. Best

(57) ABSTRACT

Methods of transferring discrete articles are provided. A method comprises providing a transfer device having a frame defining a rotation axis, and circumnavigating a plurality of transfer heads of the transfer device about the rotation axis in an orbit, with the orbit passing through a pick-up location and a drop-off location. The method comprises providing a web accumulation device proximate to the drop-off location, moving the web through the web accumulation device at a variable speed, picking up a discrete article at the pick-up location, carrying the discrete article on the one of the plurality of transfer heads between the pick-up location and the drop-off location, and placing the discrete article onto a portion of the web in the drop-off location at a first discrete article pitch and when the portion of the web is moving at a first speed.

20 Claims, 11 Drawing Sheets

(56) References Cited

U.S. PATENT DOCUMENTS

| | | |
|---|---|---|
| 8,820,513 B2 * | 9/2014 | Papsdorf ........... A61F 13/15764 198/478.1 |
| 2010/0252603 A1 | 10/2010 | Gill |
| 2011/0049210 A1 | 3/2011 | Kameda |
| 2012/0065043 A1 | 3/2012 | Lam et al. |
| 2013/0126099 A1 | 5/2013 | Gill |
| 2013/0213570 A1 * | 8/2013 | Iida ................... A61F 13/15723 156/285 |
| 2013/0248081 A1 | 9/2013 | Gill |
| 2013/0260978 A1 * | 10/2013 | Tombuelt-Meyer ........................ A61F 13/15764 493/379 |
| 2014/0109739 A1 | 4/2014 | Schneider et al. |
| 2016/0175165 A1 * | 6/2016 | Schneider ......... A61F 13/15723 604/385.3 |
| 2016/0354258 A1 | 12/2016 | Findley et al. |
| 2017/0027769 A1 | 2/2017 | Lam et al. |
| 2017/0290712 A1 | 10/2017 | Finley et al. |

\* cited by examiner

METHODS FOR TRANSFERRING DISCRETE ARTICLES

CROSS REFERENCE TO RELATED APPLICATION

This application claims the benefit, under 35 U.S.C. § 119(e), to U.S. Provisional Patent Application No. 62/520,595, filed on Jun. 16, 2017, which is hereby incorporated by reference herein in its entirety.

FIELD

The present disclosure generally relates to methods of transferring discrete articles and, more particularly, relates to methods for transferring discrete articles using web accumulation devices.

BACKGROUND

Absorbent articles, such as taped diapers or pant diapers, for example, may be manufactured by a process where discrete articles, such as a chassis of a taped diaper or a pant diaper comprising a topsheet, a backsheet, and an absorbent core, for example, are applied to one or more moving webs of components, such as webs of front and rear belt portions, or a single web of front belt portions or rear belt portions, for example. To achieve this, a transfer device may be provided that comprises one or more transfer heads and a frame defining a rotation axis. The transfer heads may circumnavigate about the rotation axis in an orbit. Each of the transfer heads may comprise a transfer surface that is configured to engage one or more of the discrete articles. The transfer heads may pick up the discrete articles at a pick-up location and place the discrete articles at a drop-off location within the orbit. In certain instances, the transfer device may rotate the discrete articles about 90 degrees, or other suitable angles, between the pick-up location and the drop-off location about a second rotation axis that is perpendicular, or substantially perpendicular, to the rotation axis. Some transfer devices that rotate and transfer discrete articles are known in the art as "turn and repitch" units because the units turn the discrete articles and repitch them (i.e., change the spacing or "pitch" between them) between the pick-up location and the drop-off location. The repitching capability of these units, however, is somewhat limited and frequent change-outs of the entire transfer devices, or portions thereof, typically must be done to transfer discrete articles having different sizes (e.g., different MD widths and/or different CD lengths). This is owing to the fact that the transfer heads of typical transfer devices circumnavigate about the rotation axis in the orbit at a constant angular velocity, thereby reducing or eliminating any pitch variation at the drop-off location. Differently sized discrete articles may require different drop off pitches at the drop-off location. Other transfer devices may not repitch the discrete articles and may merely turn them. Still other transfer devices may not repitch or turn the discrete articles and may merely transfer them. These last two categories of transfer devices still require frequent change-outs of the entire device, or portions thereof, when differently sized discrete articles are being transferred.

What is needed are methods for transferring discrete articles that significantly reduce the number of change-outs of the transfer devices, or portions thereof, when changing sizes of the discrete articles being transferred.

SUMMARY

The present disclosure solves the problem of frequent change-outs of the related art transfer devices, whether being turn and repitch units, turning units, or merely transferring units, when changing discrete article sizes. The transfer assemblies of the present disclosure each comprise a transfer device and a web accumulation device. The transfer assemblies and methods of the present disclosure solve the frequent change-out problem by providing a web accumulation device in, at least partially in, or proximate to the drop-off location of a transfer device. The web accumulation devices of the present disclosure are configured to vary the speed of a web configured to receive a portion of the discrete article upstream and downstream of the drop-off location of the transfer device, while matching or substantially matching the web speed with the speed of the transfer head carrying the discrete article in the drop-off location. The web accumulation devices essentially meter the web through the drop-off location as desired for a certain product pitch or product size. For example, a larger discrete article may require a web to move faster through the drop-off location, while a smaller discrete article may require a web to move slower through the drop-off location. Larger discrete articles may require more web accumulation in the web accumulation devices, while smaller discrete articles may require less web accumulation in the web accumulation devices. The web accumulation devices may also allow the web to move through the drop-off location at a constant speed, while varying the web speed upstream and downstream of the drop-off location. As a result, differently sized discrete articles may be transferred by a single transfer assembly without the need for changing-out the transfer device, or portions thereof.

The present disclosure is directed, in part, to a method of transferring discrete articles from a pick-up location to a drop-off location. The method may comprise providing a transfer device having a frame defining a rotation axis. The transfer device comprises a plurality of transfer heads. The method may comprise circumnavigating the plurality of transfer heads about the rotation axis in an orbit. The orbit passes through the pick-up location and the drop-off location. The method may comprise providing a web accumulation device proximate to the drop-off location, moving the web through the web accumulation device at a variable speed, and using one of the plurality of transfer heads to pick up a discrete article at the pick-up location. The method may comprise carrying the discrete article on the one of the plurality of transfer heads between the pick-up location and the drop-off location, and placing the discrete article onto a portion of the web in the drop-off location at a first discrete article pitch and when the portion of the web is moving at a first speed.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein.

DETAILED DESCRIPTION

Figure 1:
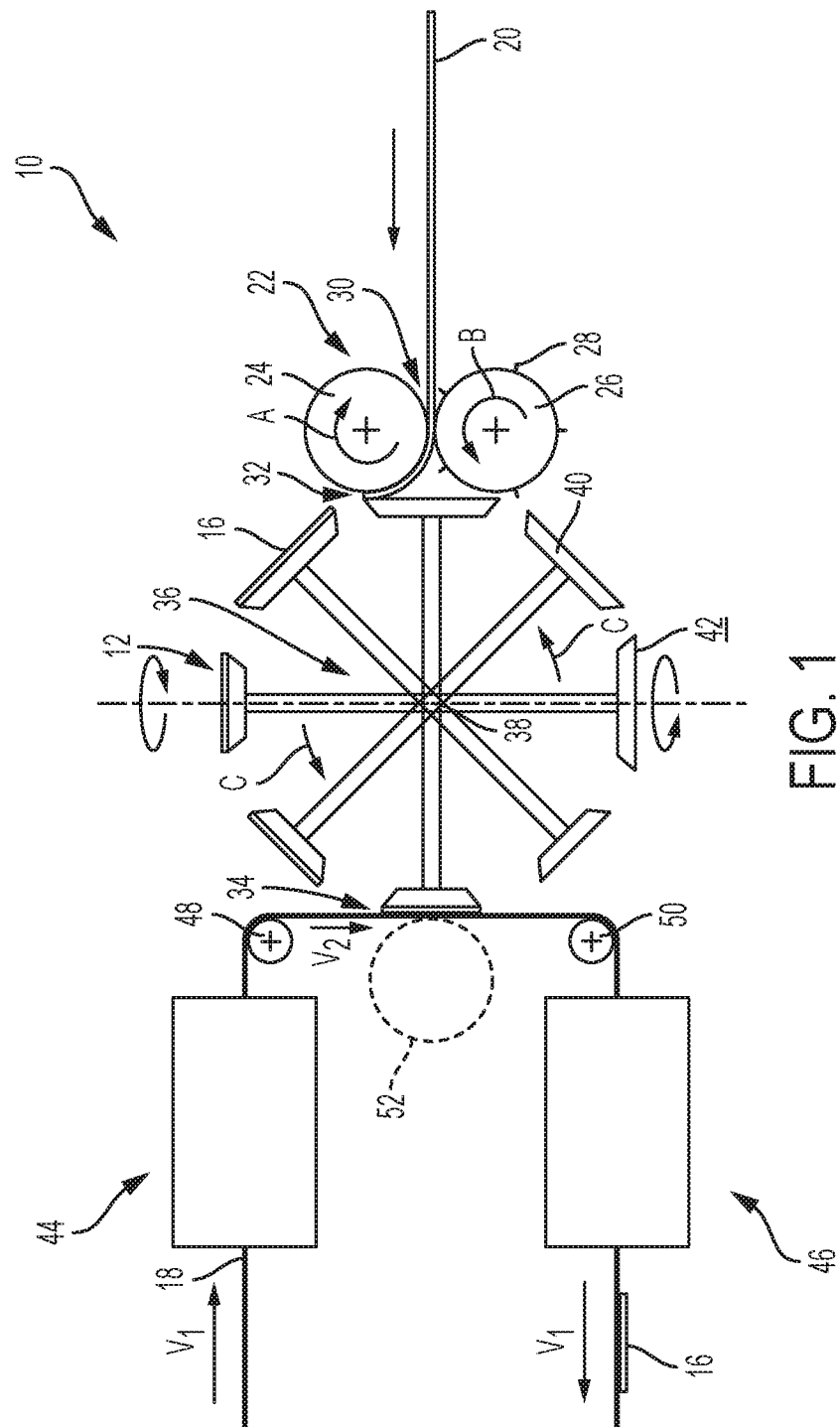
FIG. 1 is a schematic illustration of a transfer assembly comprising a transfer device and a web accumulation device, wherein the transfer device is configured to transfer discrete articles to one or more webs being conveyed by the web accumulation device.

Various non-limiting forms of the present disclosure will now be described to provide an overall understanding of the principles of the structure, function, manufacture, and use of the methods for transferring discrete articles disclosed herein. One or more examples of these non-limiting forms are illustrated in the accompanying drawings. Those of ordinary skill in the art will understand that the methods for transferring discrete articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

The term "absorbent article(s)" is used herein to refer to consumer products whose primary function is to absorb and retain bodily exudates (e.g., urine, BM, menses). Absorbent articles, as used herein, may refer to pants, taped diapers, and/or sanitary napkins (e.g., feminine hygiene products). In some instances, absorbent articles may comprise or be formed into pants, taped diapers, or sanitary napkins. The terms "diaper" and "pants" are used herein to refer to absorbent articles generally worn by infants, children, and incontinent persons, including adults, about the lower torso. The term "disposable" is used herein to describe absorbent articles which generally are not intended to be laundered or otherwise restored or reused as an absorbent article (e.g., they are intended to be discarded after a single use and may also be configured to be recycled, composted, or otherwise disposed of in an environmentally compatible manner).

The term "nonwoven" or "nonwoven material" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the primary direction of material, web, or article flow through a process. In various manufacturing and converting processes, such as a bi-fold process, it may be possible to have more than one machine direction when an article is undergoing simultaneous processes. In other words, a manufacturing line may have an overall machine direction, but a material or an article may travel in directions other than the overall machine direction as it passes through various processes along the manufacturing line. For example, a discrete article having a trailing end portion and a leading end portion, each portion being attached to the surface of a different roll and/or conveyor may travel in two different directions simultaneously. In this example, both directions of travel may be considered the machine direction.

The term "cross direction" (CD) is used herein to refer to a direction that is generally perpendicular to the machine direction.

The term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" refers herein to disposable absorbent articles having a continuous perimeter waist opening and continuous perimeter leg openings designed for infant, child, or adult wearers. A pant may be configured with a continuous or closed waist opening and at least one continuous, closed, leg opening prior to the article being applied to the wearer. A pant may be preformed by various techniques including, but not limited to, joining together portions of the absorbent article using any refastenable and/or permanent closure member (e.g., seams, heat bonds, pressure welds, adhesives, cohesive bonds, mechanical fasteners, etc.). A pant may be preformed anywhere along the circumference of the absorbent article in the waist region (e.g., side fastened or seamed, front waist fastened or seamed, rear waist fastened or seamed). A pant may be opened about one or both of the side seams and then refastened. Example pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

The term "discrete articles" refers herein to absorbent articles, pants, taped diapers, sanitary napkins, bandages, medical pads and dressings, and any other suitable articles, in any industry, capable of being transferred using the transfer apparatuses of the present disclosure. Discrete articles may also refer herein to portions of the absorbent articles, pants, taped diapers, sanitary napkins, bandages, medical pads and dressings, and other suitable articles. The discrete articles may be flexible. In one example, discrete articles may refer herein to a chassis of a taped diaper or a pant. The chassis may comprise a topsheet, a backsheet, and an absorbent core disposed between at least a portion of the topsheet and the backsheet. The chassis may comprise an acquisition layer and/or a distribution layer. The chassis may also comprise stretched elastic elements such as leg elastics and inner barrier leg cuff elastics, for example.

As referenced above, transfer assemblies comprising transfer devices and web accumulation devices and methods of using the same of the present disclosure solve the problem of transfer device change out each time a differently dimensioned discrete article is desired to be transferred. As an example, in an absorbent article context, if a size 2 diaper is being manufactured and then a size 5 diaper is desired to be manufactured, the transfer device for the size 2 diaper will not generally work to produce the size 5 diaper because of the limited pitch (i.e., product spacing) output ranges of the transfer devices. As such, the size 2 transfer device usually must be changed out with another transfer device to produce the size 5 diapers. This can result in significant downtime of the diaper manufacturing line. The present disclosure, however, solves this problem by eliminating at least some of the change outs of the transfer devices when size changes are made on a manufacturing line, owing to the ability to vary the speed of the receiving web(s) (i.e., the web(s) the discrete articles are transferred to) using a web accumulation device. Such ability allows the transfer devices to output discrete articles at a larger range of output pitches, thereby reducing change outs and, thereby, reducing manufacturing line downtime.

FIG. 1 is a schematic illustration of a transfer assembly 10 comprising a transfer device 12 and a web accumulation device 14. In general, the transfer device 12 is configured to transfer discrete articles 16 to one or more webs 18 being conveyed past a drop-off location of the transfer device 12 by the web accumulation device 14. The discrete articles 16 being transferred may be a chassis of an absorbent article, such as a diaper, a pant, or adult incontinence product. The discrete articles 16 may also be any other suitable component of an absorbent articles or other product, substrate, laminate, component, or portion thereof. The chassis of an absorbent article may comprise a topsheet, a backsheet, and an absorbent core positioned at least partially intermediate the topsheet and the backsheet. The chassis may also comprise one more acquisition material and/or distribution material at least partially intermediate the topsheet and the absorbent core. The chassis may also comprise one or more pairs of leg cuffs. The webs 18 being conveyed by the web accumulation device 14 may be front and rear belts that attach to ends of the chassis. In other instances, a single belt (e.g., a rear belt) may be attached to only one end of the chassis. The chassis and belts will be described in further detail below.

Starting on the right side of the example transfer assembly of FIG. 1, a continuous web of discrete articles 20 is conveyed toward the transfer device 12. The web of discrete articles 20 may be separated into individual discrete articles 16 by a separation device 22. The separation device may be any suitable assemblies for separating continuous webs of discrete articles 20 into discrete individual articles transfer. One example of such a separation device is illustrated in FIG. 1. The separation device 22 may comprise a transfer roll 24 and a knife roll. The transfer roll 24 may be configured to transfer discrete articles 16 to transfer heads of the transfer device 12 and may also act as an anvil for the knife roll 26. The knife roll 26 may comprise one or more knives 28 depending on the desired discrete article cut length. The knife roll 26 and the transfer roll 24 may together form a nip 30 through which the continuous web of discrete articles 20 may be conveyed to be cut into discrete articles 16. The transfer roll 24 may rotate in the direction illustrated by arrow A and the knife roll 26 may rotate in the direction illustrated by arrow B. As the knife roll 26 rotates, one of the knives 28 comes into contact with the continuous web of discrete articles 20 and presses against the transfer roll 24 to separate a single discrete article 16 and allow the single discrete article 16 to move onto one of the transfer heads of the transfer device 12. The transfer roll 24 may have vacuum to hold the discrete article thereto until transfer is desired to a transfer head. During desired transfer, the transfer roll 24 may apply a positive fluid pressure to the discrete article 16, portions thereof, to cause the discrete article 16 to transfer to a transfer head. In some instances, the transfer roll may comprise the knives and the knife roll 26 may merely act as an anvil roll. In other instances, individual discrete articles may be conveyed toward the transfer roll 24 without a separation device.

The transfer device 12 is the apparatus that is configured to turn and repitch the discrete articles 16, turn the discrete articles, or merely transfer the discrete articles 16 between a pick-up location 32 and a drop-off location 34. The transfer device 12 may comprise a frame 36 defining a rotation axis 38 and a plurality of transfer heads 40. The transfer heads 40 are configured to circumnavigate about the rotation axis 38 in an orbit. The orbit passes through the pick-up location 32 and the drop-off location 34. The transfer heads 40 may orbit in the direction illustrated by arrow C. Each of the transfer heads 40 may comprise a transfer surface 42 (i.e., discrete article receiving surface) having a plurality of fluid ports defined therein. The fluid ports are configured to provide a negative fluid pressure and/or a positive fluid pressure to the discrete articles 16 being carried on the transfer heads 40. The negative fluid pressure may be used to retain the discrete articles 16, or portions thereof, to the transfer surfaces 42 during orbiting of the transfer heads 40. The positive fluid pressure may be used to blow-off the discrete articles 16, or portions thereof, at the drop-off location 34 onto the webs 18. The transfer heads 40 may have the same speed or substantially the same speed as the transfer roll 24 in the pick-up location 32 to promote smooth transfer of the discrete articles 16.

A turn and repitch transfer device or a turning transfer device may turn the discrete articles 16 any suitable angle, in a direction perpendicular to the rotation axis 38, intermediate the pick-up location 32 and the drop-off location 34. For example, the transfer device 12 may turn the discrete articles 16 about 45 degrees, about 90 degrees, about 135 degrees, about 180 degrees, or in the range of about 40 degrees to about 200 degrees, specifically reciting all 0.5 degree increments within the specified range. The discrete articles 16 are turned by the transfer heads 40 turning. In an instance, a transfer head 40 may pick up a discrete article 16 in the pick-up location 32, turn 90 degrees about an axis perpendicular to the rotation axis 38, drop off the discrete article 16 in the drop-off location 34, and the turn back to its original position (either in the same direction or an opposite direction) before orbiting back through the pick-up location 32. In addition to the turning, the discrete articles 16 may be repitched intermediate the pick-up location 32 and the drop-off location 34. Repitching is a process where the center to center distance between articles is changed. For instance, the discrete articles 16 at the pick-up location 32 may have a pitch of 6 inches between their centers, while the discrete articles 16 at the drop-off location 34 may have a pitch of 10 inches between their centers. An example turn and repitching unit is disclosed in U.S. Pat. No. 8,820,513 to Papsdorf and Schneider. Such a unit may be useful as a transfer device of the present disclosure. The transfer devices may circumnavigate the transfer heads at a constant angular velocity or a variable angular velocity as the transfer heads orbit the rotation axis 38.

The web accumulation device 14 may be at least partially positioned in, or positioned in, the drop-off location 34. In other instances, the web accumulation device 14 may be positioned proximate to the drop-off location 34, with portions of the webs 18 being positioned in, or at least partially in, the drop-off location 34. The web accumulation devices discussed herein may take on a number of forms, some non-limiting examples of which will be discussed herein. In essence, the web accumulation devices of the present disclosure are configured to vary the speed of the one or more webs being conveyed through them such that an output pitch range of a certain transfer device may be significantly expanded. These web accumulations devices are configured to move one or more webs through portions of them at a variable speed, with the input web speed and the output web speed both being constant and the same. In most instances, only the speeds of the web or webs within portions of the web accumulation devices are varied. It some instances, it is desirable to vary the speed of the web or webs upstream and downstream of the drop-off location 34 and maintain the web or webs at a constant speed through the drop-off location 34. The speed of the webs or webs may match, or substantially match, the speed of the transfer heads 40 in the drop-off location to promote smooth discrete article transfer.

Referring to FIG. 1, the web 18 may be fed into a first portion 44 of the web accumulation device 14 at a constant velocity, V1, the first portion 44 may gather the web 18 and vary its speed (e.g., slow or increase the speed of the web), the web 18 may then be fed through the drop-off location 34 at a constant velocity, V2, that may be faster, slower, or the same as velocity, V1, depending on the desired output pitch of the discrete articles 16 being transferred. The constant velocity, V2, may match or substantially match the speed of the transfer heads 40 through the drop-off location 34. In some instances, the constant velocity, V2, may be faster than the speed of the transfer heads 40 through the drop-off location 34 to tension the discrete articles 16 being transferred and provide for smoother transfer. This is known as mis-match speed transfer. After the web 18 moves through the drop-off location 34, the web 18 may enter a second portion 46 of the web accumulation device 14. The second portion 46 of the web accumulation device 14 may also gather and vary the speed of the web 18 (e.g., slow or increase the speed of the web). In general, the second portion 46 of the web accumulation device 14 counters what the first portion 44 of the web accumulation device 14 does to the web 18. For example, if the first portion 44 gathers the web and slows it, the second portion 46 will increase the speed of the web 18. In essence, the first and second portions 44, 46 of the web accumulation device 14, in conjunction, pulse the web 18 through the drop-off location 34 at a required constant speed or at a required variable speed. The web 18 may then be outputted by the web accumulation device 14 at the constant velocity, V1.

Some web accumulation devices may be configured to handle two webs, such as front and rear belts, while other web accumulation devices may be configured to handle only one web, such as only front belts or only rear belts. In the instance where only one web may be handled, two or more web accumulation devices may be utilized if two or more receiving webs are desired in a certain processing operation.

By using a transfer assembly having a web accumulation device on an output side of a transfer device, a plurality of sizes of discrete articles may be processed without the need to change out the transfer device 12, or less frequently change out the transfer device. Stated another way, the transfer assemblies of the present disclosure allow transfer devices to process a much wider range of discrete article sizes compared to transfer assemblies without a web accumulation device.

Referring again to FIG. 1, a first guide roll 48 may be positioned proximate to the first portion 44 and a second guide roll 50 may be positioned proximate to the second portion 46. The guide roll 48 may merely be an idler roll that the web 18 runs over or may be driven rolls. In other instances, the guide rolls or one of the guide rolls may instead be stationary web guides that do not rotate. The stationary web guide may be like a fixed cylindrical pin, for example. A receiving roll 52 or other member may be positioned proximate to, in, or at least partially in, the drop-off location 34 to aid in attaching the discrete article 16 to the web 18. In other instances, the receiving roll 52 may not be provided and the discrete article 16 may be attached to the web 18 by hammock transfer between the two guide rolls 48 and 50 or stationary web guides. Adhesives or other substances may be applied (e.g., sprayed) onto the web 18 prior to the web 18 receiving the discrete articles 16 to aid in the attachment of the discrete articles 16 to the web 18. Alternatively, or in addition, the adhesives or other substances may be applied to the discrete articles 16 for the same reason. These concepts of applying adhesives or other substances and the receiving roll or member may be applied to other transfer assemblies described herein.

Figure 2:
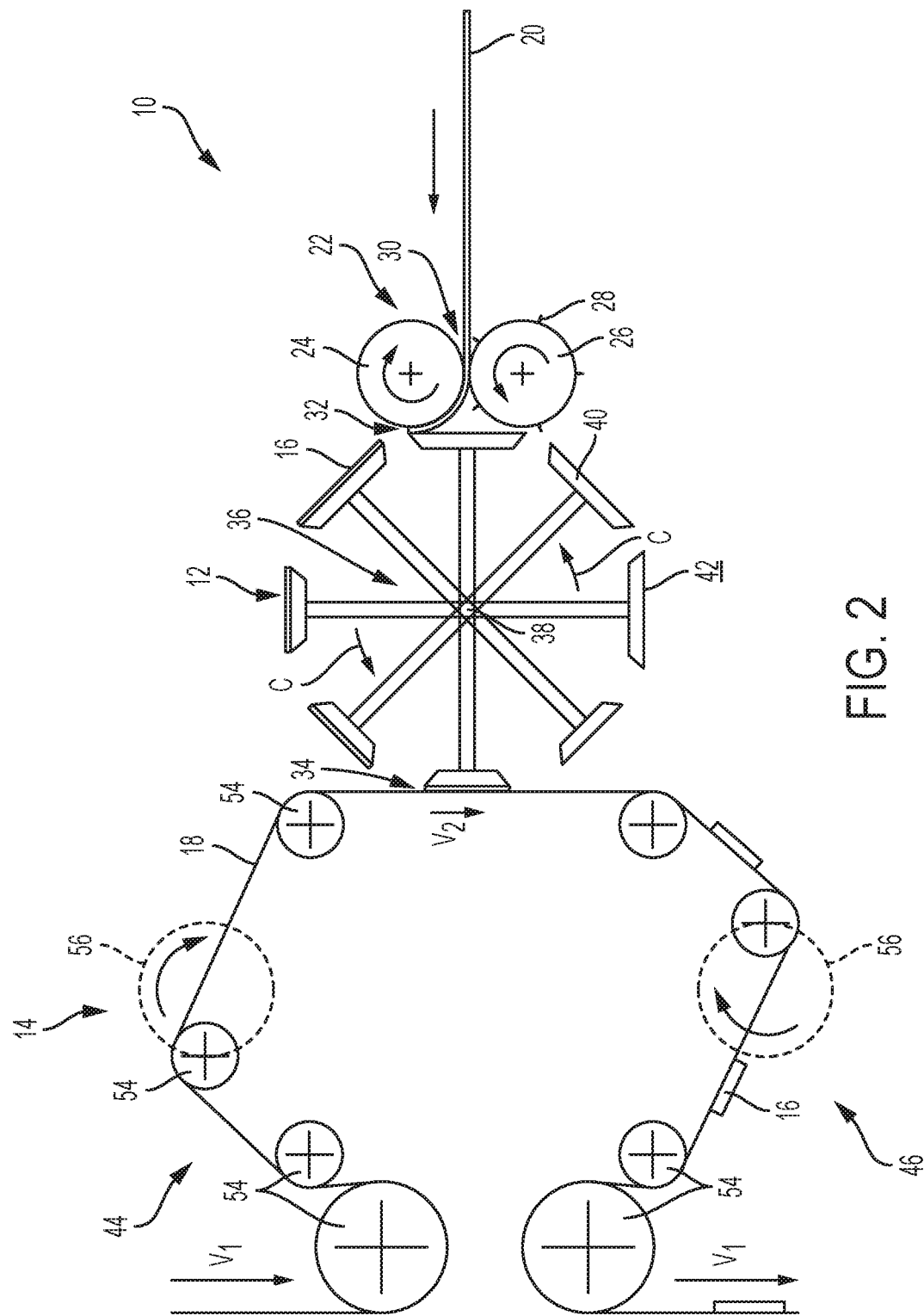
FIG. 2 is a schematic illustration of a transfer assembly comprising a transfer device and another web accumulation device, wherein the transfer device is configured to transfer discrete articles to one or more webs being conveyed by the web accumulation device.

Referring to FIG. 2, another example transfer assembly 10 is illustrated. The transfer device 12 and input equipment to the transfer device 12 may be the same or similar to that illustrated in FIG. 1. The web accumulation device 14 may comprise an eccentric accumulator. The web accumulation device 14 may comprise guide rolls 54 or stationary web guides. If guide rolls are provided, the guide rolls may be idler rolls that are fixed in position. At least some of the guide rolls may be driven rolls to move the web 18 through the web accumulation device 14. The web accumulation device 14 may comprise a first portion 44 and a second portion 46. The first and second portions 44, 46 may function and work together as described above with respect to the example of FIG. 1. Each of the first and second portions 44, 46 may comprise an eccentric 56. As illustrated, one of the guide rolls 54 in each of the first and second portions 44, 46 are fixedly mounted to the eccentric 56 while still being able to rotate. The eccentrics 56 may rotate the directions indicated by the arrows. While the eccentrics 56 rotate, they move the guide rolls 54 mounted thereto toward and away from each other, thereby moving the web 18 in the first and second portions 44, 46 towards and away from itself. This creates a variable speed in the web 18, but can still maintain a constant speed in the web 18 in the drop-off location 34. Further details regarding this concept are illustrated in U.S. Pat. No. 8,377,249B2, to Gill. The input and output web velocity, V1, to and from the web accumulation device 14 of FIG. 2 may be constant. The web velocity, V2, in the drop-off location 34 may be constant, but may be faster than, slower than, or the same as the input and output web velocity, V1. The web velocity intermediate the input side of the web accumulation device 14 and the drop-off location 34 and the web velocity intermediate the output side of the web accumulation device 14 and the drop-off location 34 may be variable.

Figure 3:
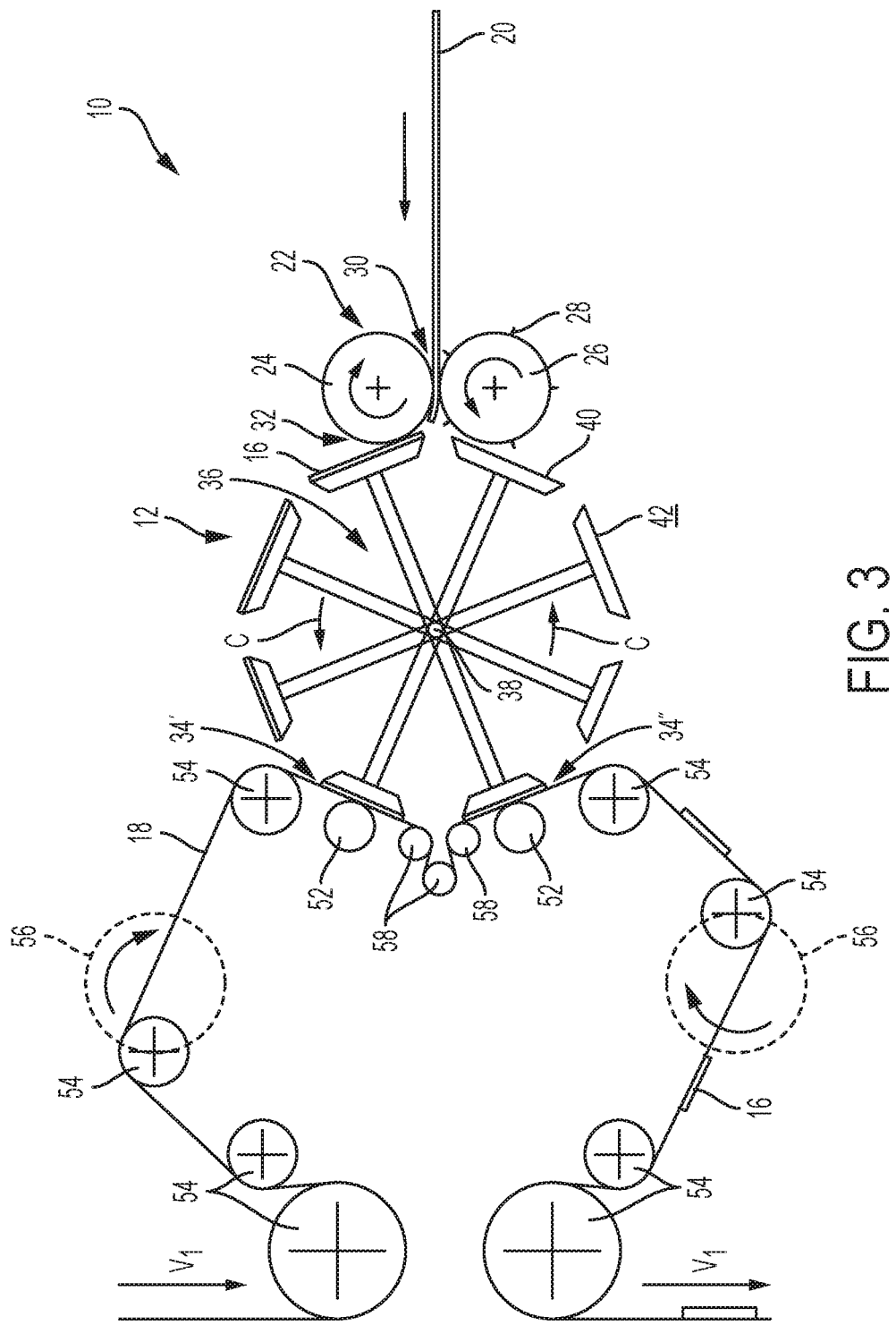
FIG. 3 is a schematic illustration of a transfer assembly comprising a transfer device and another web accumulation device, wherein the transfer device is configured to transfer two discrete articles substantially simultaneously, simultaneously, or sequentially to one or more webs being conveyed by the web accumulation device.

FIG. 3 is a modified version of the transfer assembly 10 of FIG. 2, where the transfer device 12 may place two discrete articles 16 on the web or webs 18 simultaneously, substantially simultaneously (e.g., within about 0.01 seconds to about 2 seconds of each other, specifically reciting all 0.001 second intervals within the specified range), or sequentially. If the transfer device 12 is running at a high speed (e.g., transferring over 900 discrete articles per minute), the web accumulation device 14 with a single drop-off location may not convey the web 18 fast enough to keep up with the transfer device 12. As such, in some instances, there may be a need for dual discrete article drop-off locations. By having two drop-off locations, the web accumulation device 14 can run at half the speed the transfer device 12 is running. As an example, if a transfer device 12 is transferring 1,000 discrete articles per minute, a web accumulation device only need to receive the discrete articles at a speed of 500 discrete articles per minute. The example of the web accumulation device 14 in FIG. 3 achieves this duel drop-off location by providing additional guide rolls 58 or stationary web guides intermediate a first drop-off location 34' and a second drop-off location 34". The discrete articles 16 may be transferred to the first and second drop-off locations 34' and 34" simultaneously, substantially simultaneously, or sequentially. The first and second drop-off location 34' and 34" may have receiving rolls 52. The remainder of the web accumulation device 14 and its functions may remain the same as described with respect to FIG. 2. In some instances, more than 2, such as three discrete articles may be transferred simultaneously, substantially simultaneously, or sequentially using the same concept. In this instance, the web accumulation device 14 may run at a speed of 333 discrete articles per minute if the transfer device is transferring 1,000 discrete articles per minute.

Figure 4:
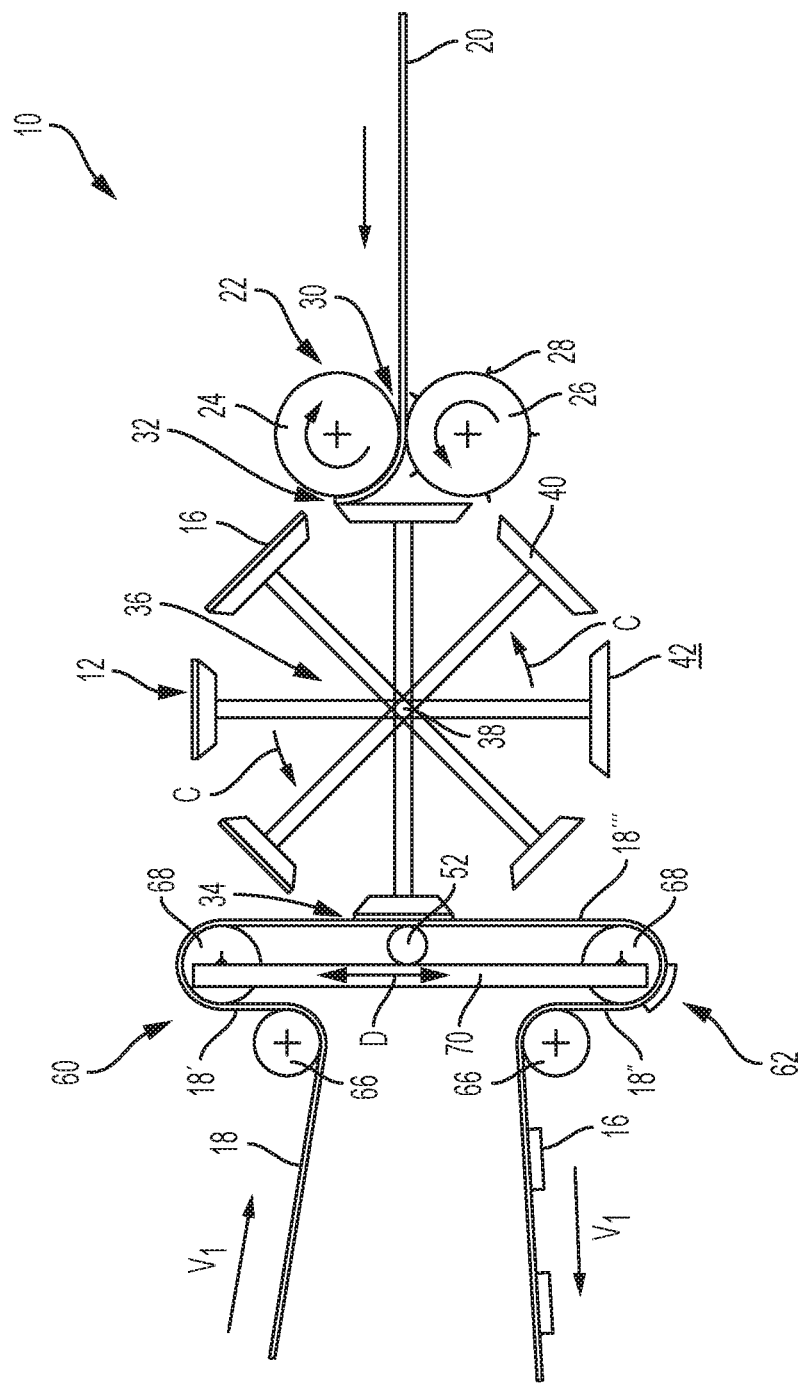
FIG. 4 is a schematic illustration of a transfer assembly comprising a transfer device and another web accumulation device, wherein the transfer device is configured to transfer discrete articles to one or more webs being conveyed by the web accumulation device.

Referring to FIG. 4, another transfer assembly 10 is illustrated. The transfer device 12 and input equipment to the transfer device 12 may be the same or similar to that illustrated in FIG. 1. The example web accumulation device 14 of FIG. 4 comprises a linear web accumulator. The web accumulation device 14 has an input side 60 and an output side 62. A web 18 is fed into the input side 60 at a constant velocity, V1, and fed out of the output side 62 at the same constant velocity. The web 18 wraps around guide rolls 66 or stationary web guides that may function as idlers or drive rolls. The guide rolls 66 or stationary web guides are fixed in position, but may be rotatable. Two transport rolls 68 are rotatably mounted on a translatable sled 70. Either or both of the transport rolls may be idler rolls or driven rolls. The sled 70 is reciprocated back and forth in the directions indicated by arrow D by any suitable type of drive motor or motors. As the sled 70 is reciprocated, portions of the web 18 intermediate the first guide roll 66 and the first transport roll 68, indicated as 18', may have a variable length and variable velocity and portions of the web 18 intermediate the second guide roll 66 and the second transport roll 68, indicated as 18", may have a variable length and a variable velocity. Portions of the web 18 intermediate the first and second transport rolls 68, indicated as 18''', may have constant length and a constant velocity. As such, when a discrete article 16 is transferred to the portion of the web 18''' the constant velocity may match or substantially match the speed of the transfer head 40 to promote smooth discrete article transfer. Although not illustrated in FIG. 4, duel discrete article transfer may also be provided in the web accumulation device 14 of FIG. 4 in a similar fashion as that illustrated by the additional guide rolls 58 of FIG. 3. Further details regarding the linear web accumulation device of the example of FIG. 4 are described in U.S. Pat. No. 6,620,276 to Kuntze et al.

Figure 5:
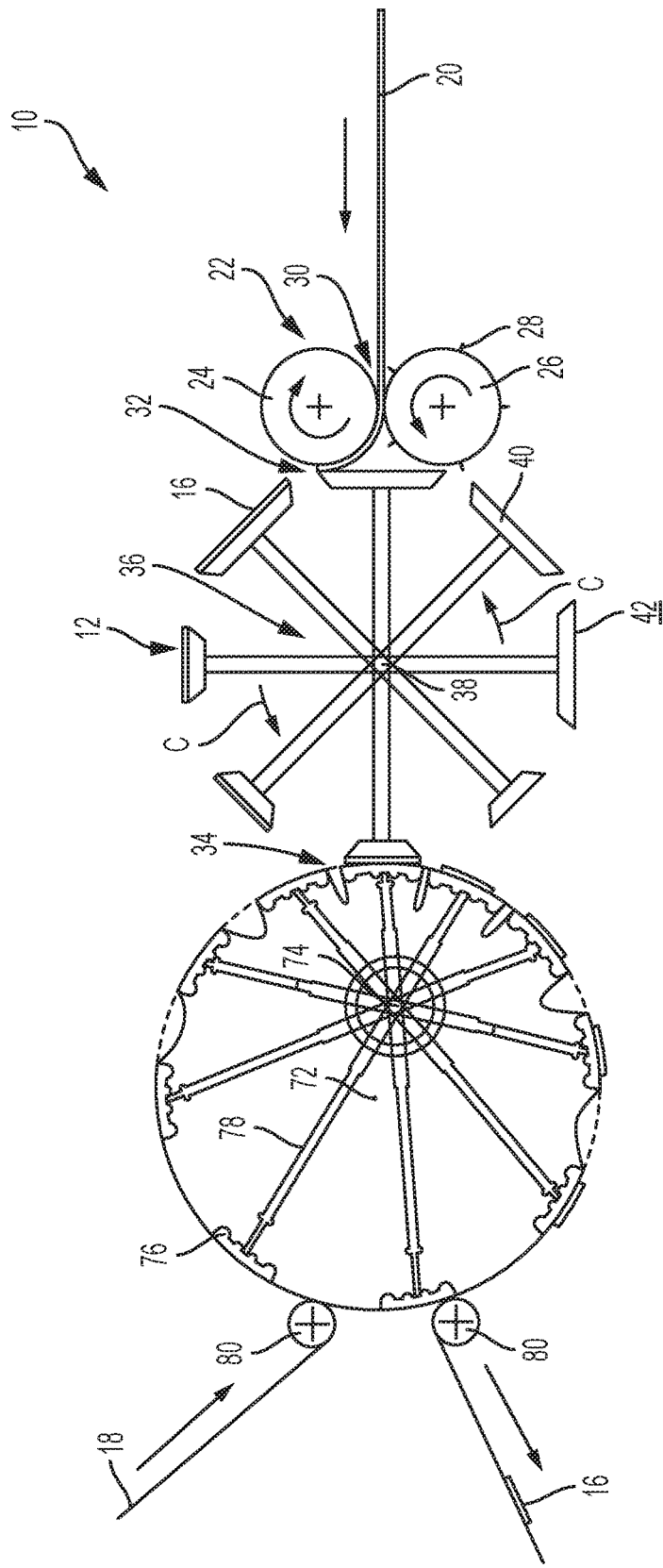
FIG. 5 is a schematic illustration of a transfer assembly comprising a transfer device and another web accumulation device, wherein the transfer device is configured to transfer discrete articles to one or more webs being conveyed by the web accumulation device.

Referring to FIG. 5, another transfer assembly 10 is illustrated. The transfer device 12 and input equipment to the transfer device 12 may be the same or similar to that illustrated in FIG. 1. The example web accumulation device 14 of FIG. 5 comprises a rotary web accumulation device. The web accumulation device 14 comprises a central axis 72 and an axis of rotation 74 offset from the central axis 82. The web accumulation device 14 may comprise a plurality of support plates 76 each mounted on a telescoping arm 78. The telescoping arms 78 are configured to expand and contract linearly to move the support plates 76 toward and away from the axis of rotation 74. The web accumulation device 14 circumnavigates the support plates 76 and the telescoping arms 78 about the axis of rotation 74. During rotation, the support plates 76 move radially toward and away from the axis of rotation 74, but maintain a constant distance away from the central axis 72. This is accomplished through the telescoping arms 78. The portions of the telescoping arms 78 proximate to the axis of rotation 74 rotate at a constant angular velocity, however, with the expansion of the telescoping arms 78, the surface speed of the support plates 76 changes. The support plates 76 will have the greatest surface speed when the telescoping arms 78 are fully extended and a slower surface speed when the telescoping arms 78 are extended the least amount.

As the support plates 76 orbit about the central axis 72, they may move from a position distal from each other to a position proximate to each other owing to the telescoping arms 78. A web 18 may enter and exit the web accumulation device 14 at points in the orbit where the support plates 76 are distal from each other. Guide rolls 80 may be fixed in position and rotatable at the input and output locations of the web accumulation device 14. Instead of guide rolls 80, stationary web guides may be provided. This causes some of the web 18 to be supported by the support plates 76 and portions of the web 18 intermediate the support plates 76 to be unsupported by the support plates 76. As the support plates 76 become closer together, the webs form a U-shape in between the support plates 76. The U-shapes are gathers or accumulations of portions of the web 18. A discrete article 16 may be transferred to a portion of the web 18 on a support plate 76 in a drop-off location while the portions of the webs 18 are in the U-shape intermediate the support plates 76. By varying the amount of the web 18 in the U-shape (or accumulated web), the web accumulation device 14, in the example of FIG. 5, allows for an increased output pitch range for the transfer device 12. The more accumulated web in the U-shape, the larger the output pitch of the transfer device 12 may be and the less accumulated web in the U-shape, the smaller the output pitch of the transfer device 12 may be. The example accumulation device of FIG. 5, owing to the U-shaped web portions, moves the web 18 through the drop-off location at a variable speed. Further details regarding the example rotary web accumulation device are described in U.S. Pat. No. 5,693,165 to Schmitz.

A method of transferring discrete articles from a pick-up location to a drop-off location may comprise providing a transfer device having a frame defining a rotation axis, wherein the transfer device comprises a plurality of transfer heads. The method may comprise circumnavigating the plurality of transfer heads about the rotation axis in an orbit. The orbit may pass through the pick-up location and the drop-off location. The method may comprise providing one or more web accumulation devices (one for each web) proximate to, in, or at least partially in to the drop-off location, moving a web through the web accumulation device at a variable speed, using one of the plurality of transfer heads to pick up a discrete article at the pick-up location, carrying the discrete article on the one of the plurality of transfer heads between the pick-up location and the drop-off location, and placing the discrete article onto a portion of the web in the drop-off location at a first discrete article pitch and when the portion of the web is moving at a first speed.

The method may comprise using a second one of the plurality of transfer heads to pick up a second discrete article at the pick-up location, carrying the second discrete article on the second one of the plurality of transfer heads between the pick-up location and the drop-off location, and placing the second discrete article onto a second portion of the web in the drop-off location at the first discrete article pitch. The two placing steps may occur simultaneously, substantially simultaneously, or sequentially.

In the event that first discrete articles with first dimensions are run on the transfer device (e.g., a size 2 diaper chassis) and then second discrete articles with second, different dimensions are desired to be run on the transfer device (e.g., a size 5 diaper chassis), the web accumulation device may vary the speed at which one or more webs are being conveyed through the drop-off location to vary the output pitch of the transfer device. Stated another way, the speed of the one or more webs through the drop-off location may be varied (e.g., increased, decreased) to vary the output pitch of the transfer device, without the need for changing out the transfer device. The method may comprise using a second one of the plurality of transfer heads to pick up a second discrete article at the pick-up location, carrying the second discrete article on the second one of the plurality of transfer heads between the pick-up location and the drop-off location, and placing the second discrete article onto a second portion of the web in the drop-off location at a second discrete article pitch and when the second portion of the web is moving at a second speed. The second discrete article's dimensions may be different than the first discrete article's dimensions. The second speed may be different than the first speed. The method may comprise maintaining a first length of the web in the web accumulation device for the first discrete article pitch and maintaining a second length of the web in the web accumulation device for the second discrete article pitch, with the first length being different than the second length.

The method may comprise matching or substantially matching the speed of the one or more webs with the speed of the transfer head during the placing steps in the drop-off location.

The method may comprise rotating the plurality of transfer heads between a first position and a second position intermediate the pick-up location and the drop-off location, wherein the rotating comprises rotating the head about 90 degrees (or other degrees) about an axis perpendicular to the rotation axis. The discrete articles may be repitched intermediate the pick-up location and the drop-off location. The method may comprise applying fluid pressure, such as vacuum or a positive pressure, to the plurality of transfer heads, or portions thereof. The method may comprise conveying the web into and out of the web accumulation device at a constant velocity.

A method may comprise transferring discrete articles from a pick-up location to a drop-off location. The method may comprise providing a transfer device having a frame defining a rotation axis. The transfer device may comprise a plurality of transfer heads. The method may comprise circumnavigating the plurality of transfer heads about the rotation axis in an orbit. The orbit may pass through the pick-up location and the drop-off location. The method may comprise providing one or more web accumulation devices (one for each web) in, at least partially in, or proximate to, the drop-off location, moving the web through the web accumulation device at a variable speed, using a first transfer head to pick up a first discrete article at the pick-up location, carrying the first discrete article on the first transfer head between the pick-up location and the drop-off location, and using a second transfer head to pick up a second discrete article at the pick-up location. The method may comprise carrying the second discrete article on the second transfer head between the pick-up location and the drop-off location, first placing the first discrete article onto a first portion of the web in the drop-off location at a first discrete article pitch and when the first portion of the web is moving at a first speed, and simultaneously or substantially simultaneously (e.g., within 0.005 to 2 seconds) with the first placing step, second placing the second discrete article onto a second portion of the web in the drop-off location at the first discrete article pitch and when the second portion of the web is moving at the first speed.

The method may comprise substantially matching the speed of the first portion of the web with the first transfer head during the first placing step and substantially matching the speed of the second portion of the web with the second transfer head during the second placing step.

The method may comprise rotating the first transfer head between a first position and a second position intermediate the pick-up location and the drop-off location. The rotating may comprise rotating the transfer head about 90 degrees about an axis perpendicular to the rotation axis. The method may comprise conveying the web into and out of the web accumulation device at a constant velocity. The method may comprise applying a fluid pressure, such as vacuum or a positive pressure, to the first and second transfer heads, or portions thereof. The method may comprise repitching the first and second discrete articles intermediate the pick-up location and the drop-off location.

A method may comprise transferring discrete articles from a pick-up location to a drop-off location. The method may comprise providing a transfer device having a frame defining a rotation axis. The transfer device may comprise a plurality of transfer heads. The method may comprise circumnavigating the plurality of transfer heads about the rotation axis in an orbit. The orbit may pass through the pick-up location and the drop-off location. The method may comprise providing one or more web accumulation devices (one for each web) in, at least partially in, or proximate to, the drop-off location, moving the web through the web accumulation device at a variable speed, and using the plurality of transfer heads to pick up first discrete articles at the pick-up location. The first discrete articles may have a first article size. The method may comprise carrying the first discrete articles on the plurality of transfer heads between the pick-up location and the drop-off location, placing the first discrete articles onto a portion of the web in the drop-off location at a first discrete article pitch and when the portion of the web is moving at a first speed. Subsequently, after transferring and placing the first discrete articles on the webs moving at the first speed, the method may comprise using the plurality of transfer heads to pick up second discrete articles at the pick-up location. The second discrete articles may have a second article size, wherein the first discrete article size may be different than the second discrete article size. The method may comprise carrying the second discrete articles on the plurality of transfer heads between the pick-up location and the drop-off location and placing the second discrete articles onto a portion of the web in the drop-off location at a second discrete article pitch and when the portion of the web is moving at a second speed. The second discrete article pitch may be different than the first discrete article pitch.

The method may comprise rotating the transfer heads between a first position and a second position intermediate the pick-up location and the drop-off location, wherein the rotating may comprise rotating the transfer heads about 90 degrees about an axis perpendicular to the rotation axis.

The method may comprise applying a fluid pressured, such as vacuum or a positive pressure, to the transfer heads and repitching the first and second discrete articles intermediate the pick-up location and the drop-off location.

Figure 6:
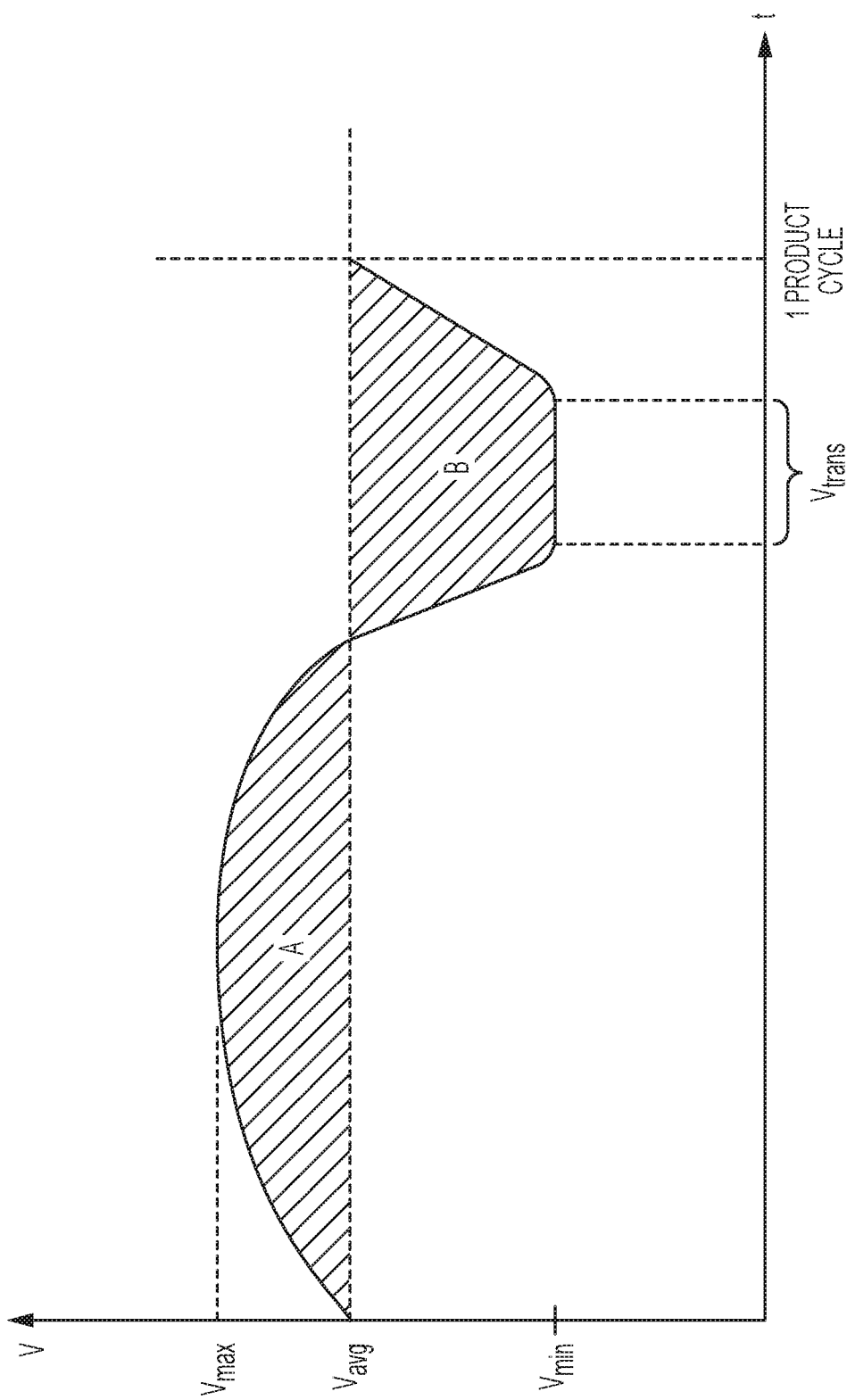
FIG. 6 is an example graphical representation of the velocity of the web configured to receive a discrete article as the web is conveyed through a web accumulation device.

FIG. 6 is an example graphical representation of the velocity of a web configured to receive a discrete article as the web is conveyed through one product cycle of the web accumulation device. The X-axis represents time, t, through one product cycle through the web accumulation device and the Y-axis represents velocity, V, of the web in the web accumulation device through one product cycle. Outside of the web accumulation device, the velocity of the web may be constant. This constant web velocity is the average web velocity, Vavg, in FIG. 6. As the web enters the web accumulation device, the web's velocity is increased (portion "A") to a maximum velocity, Vmax. Then, as the web is transported towards the drop-off location, the web's velocity is decreased (portion "B") to a minimum constant velocity, Vmin, for receiving the discrete article in the drop-off location. The transfer velocity, Vtrans, is indicated in the graph and corresponds to the minimum velocity, Vmin. It is sometimes desirable to have the transfer velocity, Vtrans, to be the same velocity as the surface speed of a transfer head 40 in the drop-off location to promote smooth discrete article transfer. The transfer velocity, Vtrans, may also be faster or slower than the surface speed of a transfer head 40 in the drop-off location in various instances. After transfer of the discrete article to the web, the velocity of the web is increased to the average web velocity, Vavg. As can be seen in the graph, the area of portion A and the area of portion B are the same such that the velocity of the web is only varied within the web accumulation device, but not outside it. Stated another way, the length of the web being inputted into the web accumulation device and the length of the web being outputted from the web accumulation device are the same.

Figure 7:
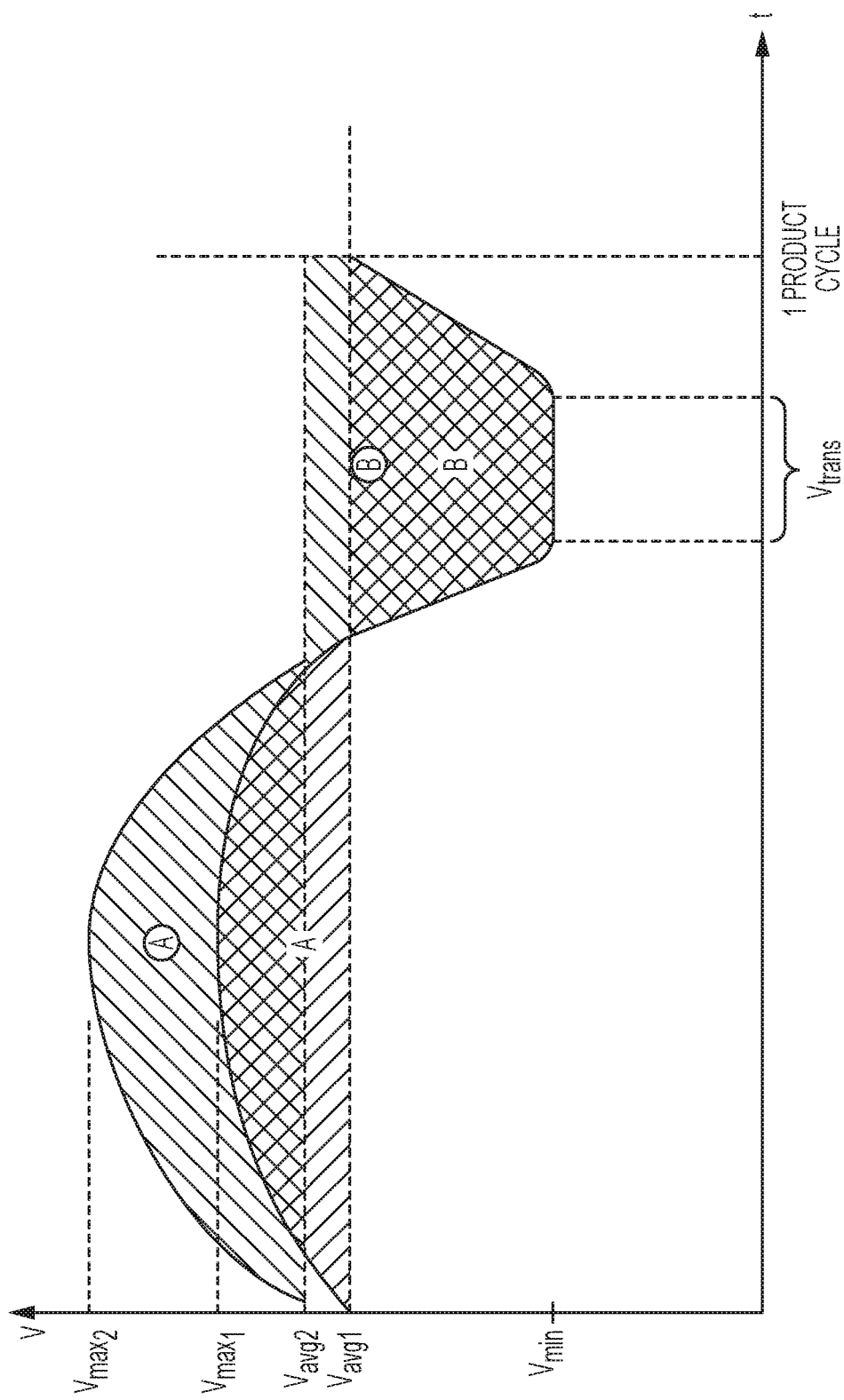
FIG. 7 is an example graphical representation of the velocity of a first web configured to receive a first discrete article with a first size as the first web is conveyed through one product cycle of a web accumulation device and the velocity of a second web configured to receive a second discrete article with a second, different size as the second web is conveyed through one cycle of the web accumulation device.

FIG. 7 is an example graphical representation of the velocity of a first web configured to receive a first discrete article having a first size as the first web is conveyed through a web accumulation device and the velocity of a second web configured to receive a second discrete article having a second, larger size as the second web is conveyed through the web accumulation device. The graph of FIG. 7 is similar to the graph of FIG. 6, but FIG. 7 illustrates two different velocity profiles configured to be run in a single web accumulation device at different times. The first web's velocity is indicated as "A" and "B" in the graph, similar to FIG. 6. The second web's velocity is indicated as A (in a circle) and B (in a circle) in the graph. The first web has less web accumulation and less web velocity change than the second web in the web accumulation device. The second web has more web accumulation and more web velocity change than the first web. The second discrete articles require a larger output pitch (from the transfer device) than the required output pitch (from the transfer device) of the first discrete articles in this instance. Vavg1 is the average web velocity of the first web outside the web accumulation device. Vavg2 is the average web velocity of the second web outside the web accumulation device. Vavg1 is slower than Vavg2. Vmax1 is the maximum velocity of the first web in the web accumulation device. Vmax2 is the maximum velocity of the second web in the web accumulation device. Vmax2 is greater than Vmax1. Vmin1 is the minimum velocity of the first web in the web accumulation device. Vmin2 is the minimum velocity of the second web in the web accumulation device. Vmin1 is the same as, or substantially the same as, Vmin2. The area A equals the area B for the first web and the area A in a circle equals the area B in a circle for the second web. The transfer velocity, Vtrans, is the same for both of the first and second webs. This enables the use of the same transfer device for differently sized discrete articles.

Figure 8:
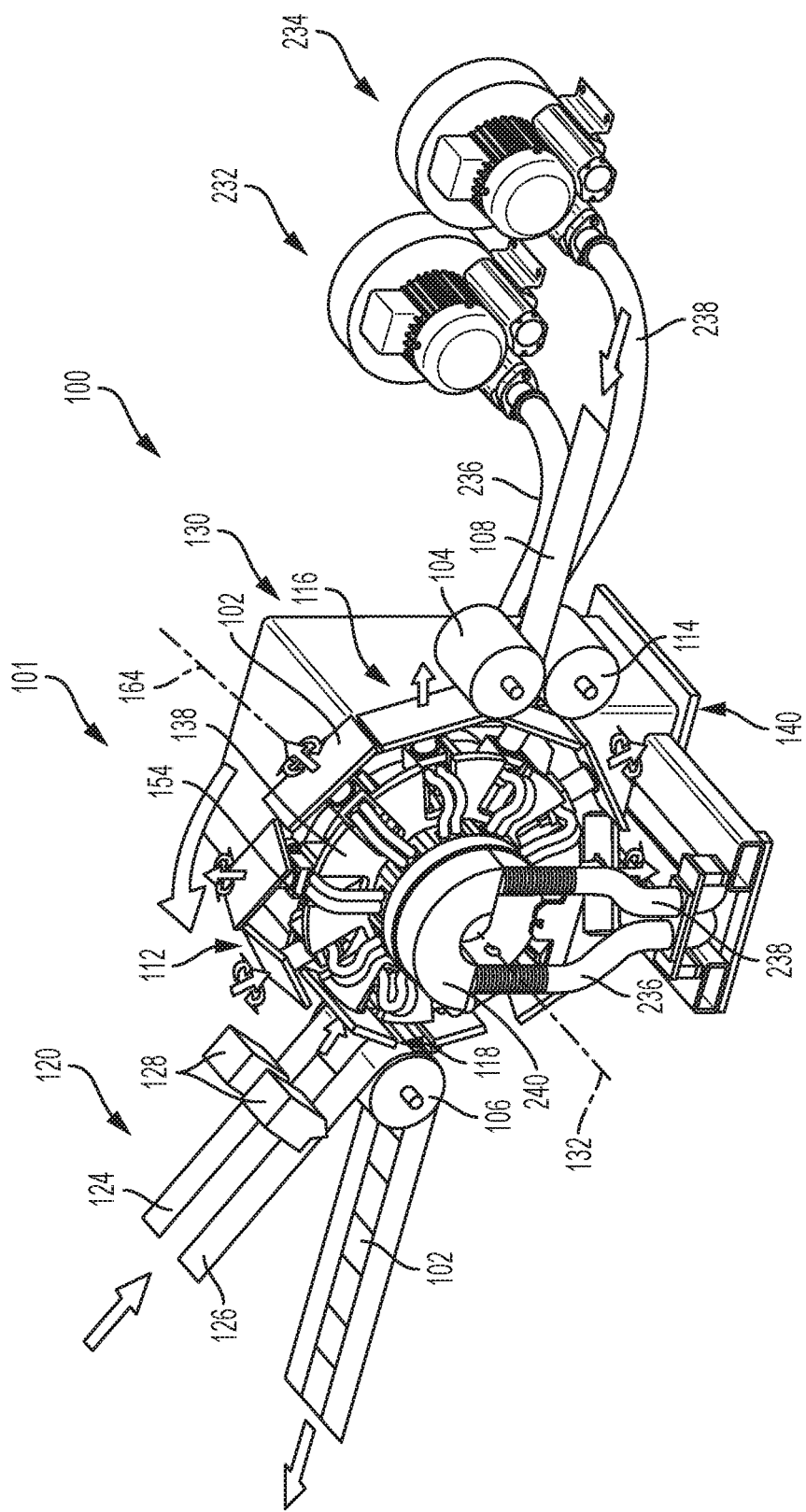
FIG. 8 is a perspective view of a turn and repitch unit configured to pick up a discrete article in a pick-up location and drop off the discrete article onto one or more webs in a drop-off location.

An example transfer assembly 100 without a web accumulation device is illustrated in FIG. 8. The transfer assembly 100 may be a turning unit or a turning and repitching unit. This transfer assembly is illustrated merely to provide an example of a transfer device and its input side. The transfer device 101 and the input side of the transfer assembly 100 may be used as the transfer device 101 of the present disclosure in combination with one or more web accumulation devices on the output side of the transfer assembly 100. In such an instance, the web accumulation device may replace the output roll 106 of the transfer device 101. The input side of the transfer device 112 may comprise an input roll 104 and an anvil roll 114. The input roll 104 and the anvil roll 114 may form a nip configured to receive a continuous web of discrete articles 108. The input roll 104 may comprise one or more knives configured to cut the continuous web of discrete articles into discrete articles 102. Together, these two rolls may be an example of a separation device 22 described herein. The transfer device 101 may comprise a frame 130 defining a first rotation axis 132 and a wheel 138 rotatable about the first rotation axis 132 with respect to the frame 130. The transfer device 101 may comprise a plurality of transfer heads 112. The transfer heads 112 each comprise a transfer surface configured to receive a discrete article. The transfer heads 112 are configured to circumnavigate about the rotation axis 132 in an orbit that passes through a pick-up location proximate to the input roll 104 and a drop-off location proximate to the output roll 106. During discrete article transfer between the pick-up location and the drop-off location, the transfer heads 112 may expand radially relative to the rotation axis 132 and turn about 90 degrees (or other degrees) about a second rotation axis 164 to turn the discrete articles 102 and repitch them for drop-off in the drop-off location. The transfer heads 112 may be in a first position 116 at the pick-up location (pre-turning) and may be in a second position 118 at the drop-off location (post-turning). The transfer heads may be flat or substantially flat. "Substantially flat," as used herein, means the transfer surface is used to support and transport a discrete article 102 conforms to a plane within about 0-10 mm, and alternatively about 0-5 mm, not including fluid ports and bolt holes.

The transfer surfaces of the transfer heads 112 may define a plurality of fluid ports therein. A first fluid movement device 232 may be in fluid communication with a first fluid line 236 and a second fluid movement device 234 may be in fluid communication with a second fluid line 238. Both of the fluid lines 236, 238 may supply fluid to a fluid receiving manifold 240. Fluids may be supplied to the fluid ports in the transfer surfaces of the transfer heads 112 through fluid lines that extend from the fluid manifold 240 to the transfer heads 112 through recesses defined in the wheel 138. One of the fluid movement devices may supply a positive fluid pressure and the other fluid movement device may supply a negative fluid pressure, or both may cycle between supplying a positive fluid pressure and negative fluid pressure. The negative fluid pressure may be used to maintain the discrete articles 102 on the transfer surfaces and the positive fluid pressure may be used to blow-off the discrete articles from the transfer surfaces in the drop-off location.

Two webs 124 and 126 are illustrated being conveyed around the output roller 106. These two webs 124 and 126 may be front and back belts for a pant and the discrete article being transferred may be a pant chassis, for example. These webs 124 and 126, or at least one of them, may be conveyed through the web accumulation devices herein to provide additional output pitch ranges for the transfer device 101. An example of adhesive dispensers 128 for the webs 124 and 126 are also illustrated in FIG. 8.

Figure 9:
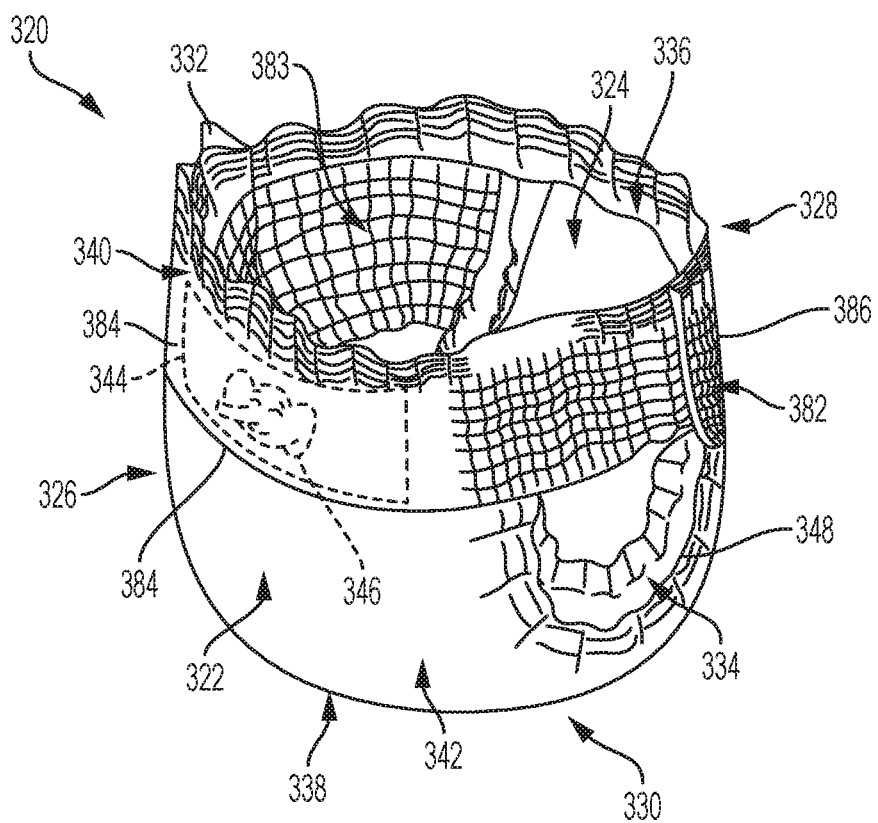
FIG. 9 is a perspective front view of an example discrete article that is a pant.
Figure 10:
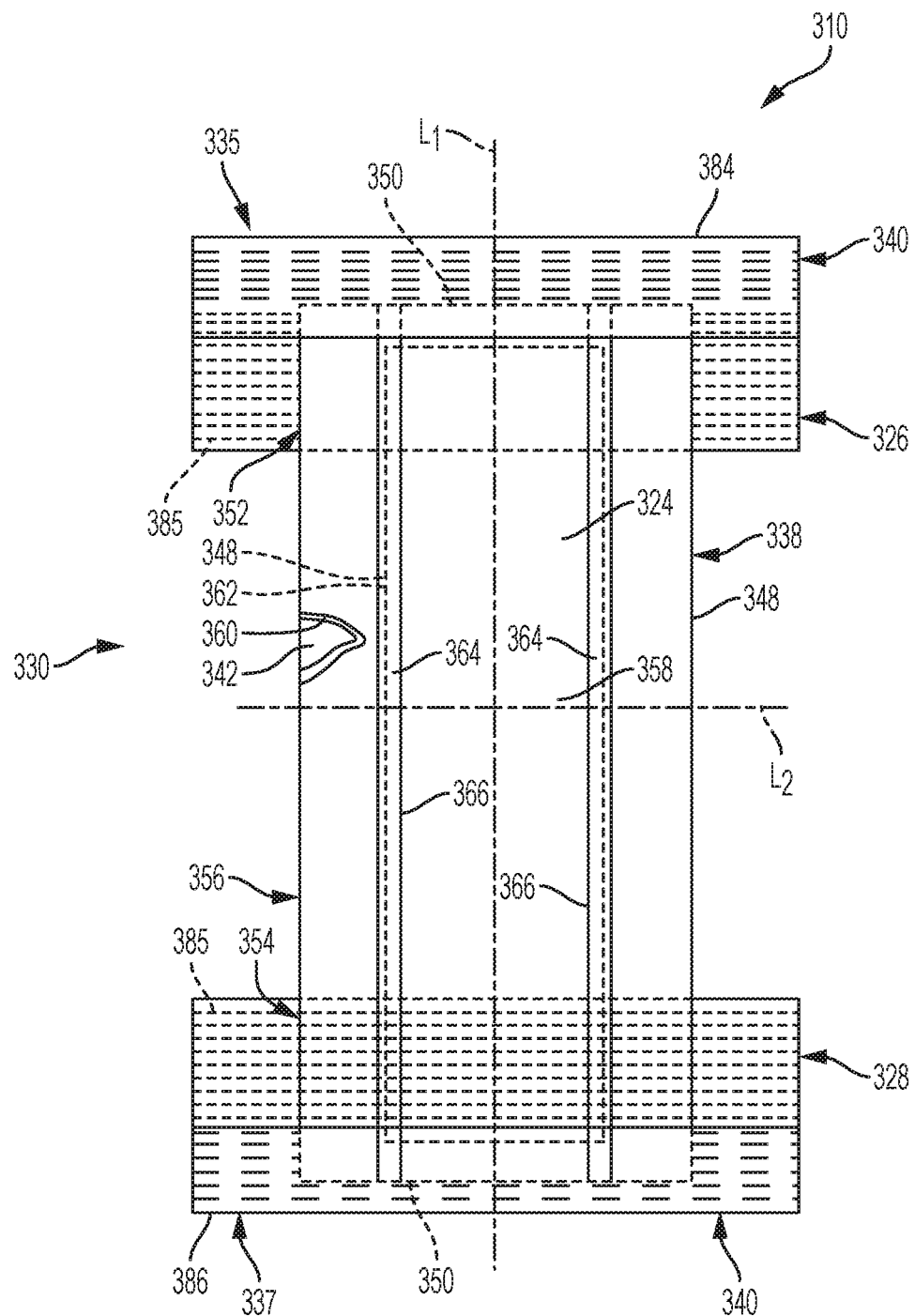
FIG. 10 is a plan view of the example pant of FIG. 9, with elastic contraction pulled out and with the side seams separated or opened, wearer-facing surface facing the viewer.

FIG. 9 illustrates an example of a pant 320 that may be at least partially formed or manufactured using the transfer assemblies 10 of the present disclosure. FIG. 10 illustrates an absorbent article 310 that can be formed into the pant 320 of FIG. 8. Those of skill in the art will recognize that FIGS. 9 and 10 are merely examples of one product that may be formed, or at least partially manufactured, using the transfer assemblies of the present disclosure. Many other products, including other absorbent articles, pants, or portions thereof, may be formed, or at least partially manufactured, using the transfer assemblies of the present disclosure. The absorbent article 310 has a longitudinal central axis L1 and a lateral central axis L2 (see FIG. 10). The pant 320 has an outer surface 322, an inner surface 324 opposed to the outer surface 322, a front waist region 326, a rear waist region 328, a crotch region 330, and seams 332 which join the front waist region 326 and the rear waist region 328 to form two leg openings 334 and a waist opening 336. The seams 332 may be permanent or refastenable. When referring to "pant 320" herein, it will be understood that the absorbent article 10, although not yet formed into the pant 320, may be considered a "pant". It will be understood that the pant 320 is disclosed as an example, but that a taped diaper may also be formed from the absorbent article 310 merely by adding fastening elements and/or landing zones to one or both of the front and rear belts 384 and 386.

The pant 320 may comprise an absorbent chassis 338 to cover a crotch region of a wearer and a belt 340 extending transversely about the waist opening 336. The pant 320 may also optionally comprise an outer cover layer 342 to cover the chassis 338. The belt 340 may define the waist opening 336 in the pant 320. The belt 340, the chassis 338, and/or the outer cover layer 342 may jointly define the leg openings 334. The pant 320 may have a patch sheet 344 printed with a graphic 346 thereon, which may be disposed in the front waist region 326, the rear waist region 328, or any other suitable portion of the pant 320. The belt 340 may be formed from a front belt 384 in the front waist region 326 and a rear belt 386 in the rear waist region 328. The front belt 384 may form a front waist edge 335 in the front waist region 326 and the rear belt 386 may form a rear waist edge 337 in the rear waist region 328. The front and rear waist edges 335 and 337 may be laterally opposed about the lateral central axis L2. The belt 340 may form a portion of an outer surface 322 or an inner surface 324 of the pant 320. In other forms, the belt 340, or portions thereof, may be disposed intermediate other layers of the chassis 338, such as a topsheet and a backsheet, for example.

The absorbent chassis 338 may absorb and contain body exudates or wastes disposed on the chassis 338. Referring to FIG. 10, the chassis 338 may have a generally rectangular shape having left and right longitudinally extending side edges 348 (hereinafter may be referred to as "longitudinal side edge") and front and rear laterally extending end edges 350 (hereinafter may be referred to as "lateral end edge"). The chassis 338 may also comprise waist panels (i.e., a front waist panel 352 positioned in the front waist region 326 and a rear waist panel 354 positioned in the rear waist region 328) and a crotch panel 356 in the crotch region 330 between the front and rear waist panels 352, 354.

Referring to FIG. 10, the pant 320 may comprise front and rear belts 384 and 386 intended to encircle at least a portion of the waist of the wearer. The front and rear belts 384 and 386 together form at least a portion of, or all of, the belt 340 when joined. The front and rear belts 384 and 386 may be formed from portions of the webs being conveyed through the web accumulation devices of the present disclosure. The front and rear belts 384 and 386 may be connected by the chassis 338 forming the crotch region 330 of the pant 320. The front and rear belts 384 and 386 may each be formed from a first belt layer 382 possibly forming a portion of the outer surface 322 of the pant 320 and a second belt layer 383 possibly forming a portion of the inner surface 324 of the pant 320. The first and second belt layers 382 and 383 may be comprised of any suitable materials. Various suitable materials may comprise films, plastic films, apertured plastic films, woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers, stretchable nonwovens, or coated woven or nonwoven webs. The belt 340 may comprise an inner hydrophobic, nonwoven material and an outer hydrophobic, nonwoven material. The front and rear belts 384 and 386 may also comprise a plurality of elastic elements 385 disposed at least partially between the first and second belt layers 382 and 383 thereof and attached to at least one of the first and second belt layers 382 and 383 using adhesives or bonding, for example. The elastic elements 385 may comprise one or more elastic strands, elastic materials, elastomeric films, elastomeric ribbons, elastomeric nonwovens, elastomeric filaments, elastomeric adhesives, elastomeric foams, scrims, or combinations thereof The chassis 338 of the pant 320 may comprise a portion of the outer surface 322, a backsheet 360, a portion of the inner surface 324, a topsheet 358, and an absorbent core 362 disposed between at least a portion of the topsheet 358 and the backsheet 360. In addition, the chassis 338 may comprise elasticized barrier leg cuffs 364 disposed at or adjacent the side edges 348 of the chassis 338. The barrier leg cuffs 364 may provide improved containment of liquids and other body exudates or wastes in the crotch region 330 and may comprise a single layer of material which may be folded to form a barrier leg cuff having two layers. The barrier leg cuffs 364 may extend from the side of the chassis 338 at or adjacent the longitudinal side edge 348 toward the longitudinal central axis L1. The barrier leg cuffs 364 may be folded along the folding lines 366 back toward the longitudinal side edges 348. The front and rear belts 384 and 386 may overlap at least a portion of the chassis 338 and one or both of the front and rear belts 384 and 386 may be disposed on the outer surface 322 of the chassis 338, on the inner surface 324 of the chassis 338, or disposed intermediate various portions of the chassis 338.

The liquid pervious topsheet 358 may be positioned adjacent the body-facing surface of the absorbent core 362 and may be joined thereto and/or to the backsheet 360 by any suitable attachment means known to those of skill in the art. The liquid impervious backsheet 360 may generally be that portion of the pant 320 positioned adjacent the garment-facing surface of the absorbent core 362 and may prevent, or at least inhibit, the bodily exudates and wastes absorbed and contained in the absorbent core 362 from soiling garments that may contact the outer surface 322 of the pant 230.

The topsheet 358, the backsheet 360, and the absorbent core 362 may be manufactured of any suitable materials. Suitable topsheet materials may comprise porous foams; reticulated foams; apertured plastic films; nonwoven materials; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the pant 320 while still preventing, or at least inhibiting, bodily exudates or wastes from passing through the backsheet 360. Such materials may include nonwoven materials, woven materials, films, and/or laminates comprising a combination of one or more of these materials. In one form, the backsheet 360 may be a film and nonwoven laminate, wherein the nonwoven of the laminate forms the outer cover layer 342.

A suitable absorbent core 362 for use in the pant 320 may comprise any absorbent material which is generally compressible, conformable, non-irritating to the wearer's skin, and capable of absorbing and retaining liquids such as urine and other certain body exudates. In addition, the configuration and construction of the absorbent core 362 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some forms, the absorbent core 362 may comprise a fluid acquisition component, a fluid distribution component, and/or a fluid storage component. An example of a suitable absorbent core having a fluid acquisition component, a fluid distribution component, and a fluid storage component is described in U.S. Pat. No. 6,590,136. The absorbent cores comprise an absorbent material that may be positioned in a core bag. The core bag may form a C-wrap. The absorbent material may comprise a superabsorbent material and airfelt, only airfelt, or only superabsorbent materials. Adhesives are not considered to be "absorbent materials."

The outer cover layer 342 may be disposed on the outer surface 322 of the pant 320 and may cover the crotch panel 356 of the absorbent chassis 338. The outer cover layer 342 may extend into and cover the front waist panel 352 and the rear waist panel 354 of the chassis 338. The outer cover layer 342 may form a portion of the backsheet 360 and/or the chassis 338. The outer cover layer 342 may be directly joined to and cover a portion of, or all of, the liquid impervious backsheet 360 of the chassis 338. The outer cover layer 342 may be disposed between the front and rear belts 384 and 386.

The outer cover layer 342 may comprise a material separate from the first and second belt layers 382 and 383 forming the belts 384 and 386. The outer cover layer 342 may comprise two or more layers of materials of any known materials including the materials used for the first and second belt layers 382 and 383. The outer cover layer 342 may comprise a single layer of a nonwoven web of synthetic fibers. The outer cover layer 342 may comprise a single layer of hydrophobic, non-stretchable nonwoven material. The outer cover layer 342 may comprise a film, a foam, a nonwoven, a woven material, or the like and/or combinations thereof such as a laminate of a film and a nonwoven.

The belt 340 may be at least partially formed, or fully formed, when the front and rear belts 384 and 386 are permanently or refastenably connecting together to form the seams 332. Any suitable seams may be formed, as known to those of skill in the art, such as butt seams and overlap seams. The belt 340 may be ring-like and elastic. The ring-like elastic belt 340 may extend about the waist opening 336 of the pant 320 and act to dynamically create fitment forces and to distribute the forces dynamically generated during wear.

Figure 11:
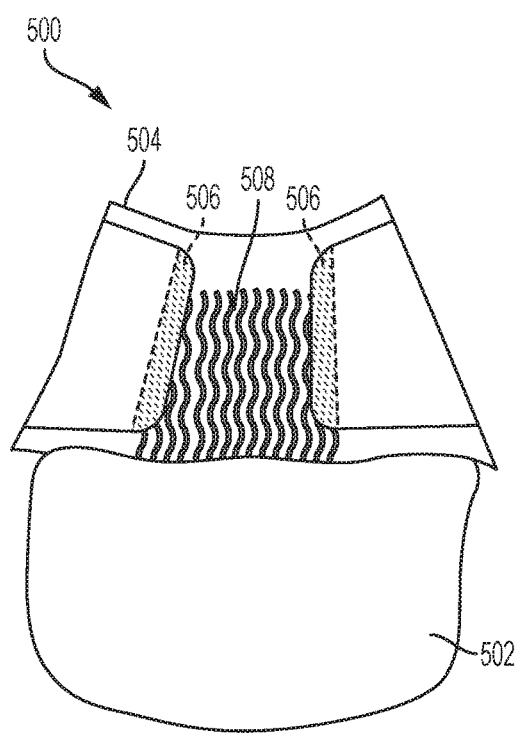
FIG. 11 is a front view of an example discrete article that is a single belted article with front fastening, in a fastened configuration.
Figure 12:
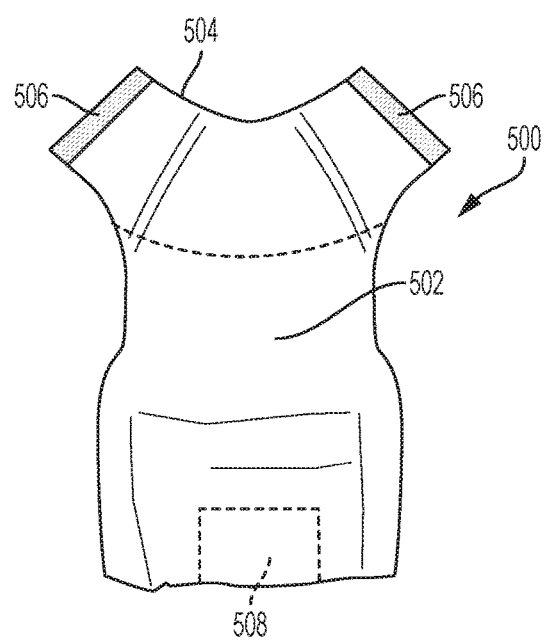
FIG. 12 is a plan view of the example single belted article of FIG. 11, with elastic contraction pulled out and in an unfastened configuration, wearer-facing surface facing the viewer.

FIGS. 11 and 12 illustrate another type of absorbent article 500 that may be manufactured using the transfer assemblies 10 of the present disclosure. The absorbent article 500 may comprise a chassis 502 comprising a topsheet, a backsheet, and an absorbent core at least partially intermediate the topsheet and the backsheet. The chassis may comprise an outer cover nonwoven material positioned on the garment-facing side and one or more optional acquisition and distribution materials intermediate the topsheet and the absorbent core. The absorbent article 500 may comprise a single belt 504 attached to a rear region of the chassis 502. The single belt 504 may be a web 18 that is conveyed through the web accumulation devices described herein.

The single belt 504 may comprise fasteners 506 that fasten to portions of the outer cover nonwoven material or to a landing zone 508 in the front region of the chassis 502.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any forms disclosed or claimed herein or that it alone, or in any combination with any other reference or references, teaches, suggests or discloses any such form. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of transferring discrete articles from a pick-up location to a drop-off location, the method comprising:
   providing a transfer device having a frame defining a rotation axis, wherein the transfer device comprises a plurality of transfer heads;
   circumnavigating the plurality of transfer heads about the rotation axis in an orbit, wherein the orbit passes through the pick-up location and the drop-off location;
   providing a web accumulation device proximate to the drop-off location, wherein the web accumulation device is configured to convey a web;
   moving the web through the web accumulation device at a variable speed;
   using one of the plurality of transfer heads to pick up a discrete article at the pick-up location;
   carrying the discrete article on the one of the plurality of transfer heads between the pick-up location and the drop-off location; and
   placing the discrete article onto a portion of the web in the drop-off location at a first discrete article pitch and when the portion of the web is moving at a first speed.

2. The method of claim 1, comprising:
   using a second one of the plurality of transfer heads to pick up a second discrete article at the pick-up location;
   carrying the second discrete article on the second one of the plurality of transfer heads between the pick-up location and the drop-off location; and
   placing the second discrete article onto a second portion of the web in the drop-off location at the first discrete article pitch, wherein the two placing steps occur substantially simultaneously.

3. The method of claim 1, comprising:
   using a second one of the plurality of transfer heads to pick up a second discrete article at the pick-up location;
   carrying the second discrete article on the second one of the plurality of transfer heads between the pick-up location and the drop-off location; and
   placing the second discrete article onto a second portion of the web in the drop-off location at the first discrete article pitch, wherein the two placing steps occur sequentially.

4. The method of claim 1, comprising:
   using a second one of the plurality of transfer heads to pick up a second discrete article at the pick-up location;
   carrying the second discrete article on the second one of the plurality of transfer heads between the pick-up location and the drop-off location; and
   placing the second discrete article onto a second portion of the web in the drop-off location at a second discrete article pitch and when the second portion of the web is moving at a second speed, wherein the second discrete article's dimensions are different than the first discrete article's dimensions.

5. The method of claim 4, wherein the second speed is different than the first speed.

6. The method of claim 4, comprising:
   maintaining a first length of the web in the web accumulation device for the first discrete article pitch; and
   maintaining a second length of the web in the web accumulation device for the second discrete article pitch;
   wherein the first length is different than the second length.

7. The method of claim 1, comprising substantially matching the speed of the web with the speed of the transfer head during the placing step.

8. The method of claim 1, comprising rotating the plurality of transfer heads between a first position and a second position intermediate the pick-up location and the drop-off location.

9. The method of claim 8, wherein the rotating comprises rotating the head about 90 degrees about an axis perpendicular to the rotation axis.

10. The method of claim 1, comprising repitching the discrete articles intermediate the pick-up location and the drop-off location.

11. The method of claim 1, comprising applying a fluid pressure to the plurality of transfer heads.

12. The method of claim 1, comprising conveying the web into and out of the web accumulation device at a constant velocity.

13. A method of transferring discrete articles from a pick-up location to a drop-off location, the method comprising:
   providing a transfer device having a frame defining a rotation axis, wherein the transfer device comprises a plurality of transfer heads;
   circumnavigating the plurality of transfer heads about the rotation axis in an orbit, wherein the orbit passes through the pick-up location and the drop-off location;
   providing a web accumulation device at least partially in the drop-off location, wherein the web accumulation device is configured to convey a web;
   moving the web through the web accumulation device at a variable speed;
   using a first transfer head to pick up a first discrete article at the pick-up location;
   carrying the first discrete article on the first transfer head between the pick-up location and the drop-off location;
   using a second transfer head to pick up a second discrete article at the pick-up location;
   carrying the second discrete article on the second transfer head between the pick-up location and the drop-off location;
   first placing the first discrete article onto a first portion of the web in the drop-off location at a first discrete article pitch and when the first portion of the web is moving at a first speed; and
   substantially simultaneously with the first placing step, second placing the second discrete article onto a second portion of the web in the drop-off location at the first discrete article pitch and when the second portion of the web is moving at the first speed.

14. The method of claim 13, comprising:
   substantially matching the speed of the first portion of the web with the first transfer head during the first placing step; and
   substantially matching the speed of the second portion of the web with the second transfer head during the second placing step.

15. The method of claim 13, comprising rotating the first transfer head between a first position and a second position intermediate the pick-up location and the drop-off location, wherein the rotating comprises rotating the transfer head about 90 degrees about an axis perpendicular to the rotation axis.

16. The method of claim 13, comprising:
conveying the web into and out of the web accumulation device at a constant velocity; and
applying a fluid pressure to the first and second transfer heads.

17. The method of claim 13, comprising repitching the first and second discrete articles intermediate the pick-up location and the drop-off location.

18. A method of transferring discrete articles from a pick-up location to a drop-off location, the method comprising:
providing a transfer device having a frame defining a rotation axis, wherein the transfer device comprises a plurality of transfer heads;
circumnavigating the plurality of transfer heads about the rotation axis in an orbit, wherein the orbit passes through the pick-up location and the drop-off location;
providing a web accumulation device at least partially in the drop-off location, wherein the web accumulation device is configured to convey a web;
moving the web through the web accumulation device at a variable speed;
using the plurality of transfer heads to pick up first discrete articles at the pick-up location, wherein the first discrete articles have a first discrete article size;
carrying the first discrete articles on the plurality of transfer heads between the pick-up location and the drop-off location;
placing the first discrete articles onto a portion of the web in the drop-off location at a first discrete article pitch and when the portion of the web is moving at a first speed;
subsequently, the method comprises:
using the plurality of transfer heads to pick up second discrete articles at the pick-up location, wherein the second discrete articles have a second discrete article size, and wherein the first discrete article size is different than the second discrete article size;
carrying the second discrete articles on the plurality of transfer heads between the pick-up location and the drop-off location; and
placing the second discrete articles onto a portion of the web in the drop-off location at a second discrete article pitch and when the portion of the web is moving at a second speed, wherein the second discreet article pitch is different than the first discrete article pitch.

19. The method of claim 18, comprising rotating the transfer heads between a first position and a second position intermediate the pick-up location and the drop-off location, wherein the rotating comprises rotating the transfer heads about 90 degrees about an axis perpendicular to the rotation axis.

20. The method of claim 18, comprising:
applying a fluid pressure to the transfer heads; and
repitching the first and second discrete articles intermediate the pick-up location and the drop-off location.

* * * * *